(12) United States Patent
Oishi et al.

(10) Patent No.: US 7,087,168 B2
(45) Date of Patent: Aug. 8, 2006

(54) HOLLOW FIBER MEMBRANE FOR PURIFYING BLOOD

(75) Inventors: Teruhiko Oishi, Miyazaki (JP); Tomoji Hanai, Miyazaki (JP)

(73) Assignee: Asahi Kasei Medical Co., Ltd., Tokyo (JP)

( * ) Notice: Subject to any disclaimer, the term of this patent is extended or adjusted under 35 U.S.C. 154(b) by 0 days.

(21) Appl. No.: 10/484,712

(22) PCT Filed: Jul. 24, 2002

(86) PCT No.: PCT/JP02/07501

§ 371 (c)(1),
(2), (4) Date: May 19, 2004

(87) PCT Pub. No.: WO03/009926

PCT Pub. Date: Feb. 6, 2003

(65) Prior Publication Data

US 2004/0206692 A1    Oct. 21, 2004

(30) Foreign Application Priority Data

Jul. 24, 2001  (JP)  ............................. 2001-222445
Jul. 24, 2001  (JP)  ............................. 2001-222446

(51) Int. Cl.
*B01D 33/21*  (2006.01)
*B01D 39/00*  (2006.01)
*B01D 39/14*  (2006.01)

(52) U.S. Cl. ..................... 210/500.23; 210/500.42; 210/500.27; 210/500.41; 264/41; 264/177.14; 264/177.26; 264/48; 264/176.1

(58) Field of Classification Search ........... 210/500.23, 210/500.41, 500.42, 645, 644, 500.27; 264/41, 264/177.14, 171.26, 178, 48, 176.1, 177.26
See application file for complete search history.

(56) References Cited

U.S. PATENT DOCUMENTS

| | | | | |
|---|---|---|---|---|
| 3,871,950 A | * | 3/1975 | Hashino et al. | 428/398 |
| 4,882,223 A | * | 11/1989 | Aptel et al. | 428/398 |
| 5,089,192 A | * | 2/1992 | Costa | 264/49 |
| 5,232,597 A | * | 8/1993 | Eguchi | 210/500.23 |
| 5,232,601 A | * | 8/1993 | Chu et al. | 210/646 |
| 5,340,480 A | * | 8/1994 | Kawata et al. | 210/500.23 |
| 5,683,584 A | * | 11/1997 | Wenthold et al. | 210/500.23 |
| 5,762,798 A | * | 6/1998 | Wenthold et al. | 210/500.23 |
| 5,938,929 A | * | 8/1999 | Shimagaki et al. | 210/645 |
| 6,074,718 A | * | 6/2000 | Puglia et al. | 428/36.5 |
| 6,165,363 A | * | 12/2000 | Oishi et al. | 210/500.23 |
| 6,596,167 B1 | * | 7/2003 | Ji et al. | 210/500.42 |

FOREIGN PATENT DOCUMENTS

| | | | |
|---|---|---|---|
| EP | 1110563 | | 12/2000 |
| JP | 63 097205 A | | 4/1988 |
| JP | 10 066846 A | | 2/2001 |
| WO | WO 02/058828 | * | 8/2002 |

* cited by examiner

Primary Examiner—Ana Fortuna
(74) Attorney, Agent, or Firm—Young & Thompson

(57) ABSTRACT

It is intended to provide a blood purification membrane having excellent performance and showing little elution of blood and little adhesion of blood proteins or platelets. The above object can be achieved by using a moisten membrane, which is free from any membrane pore-sustaining agent and has a high water permeation dose and a large pore size, and lessening the pore size by drying the membrane after desolvation.

10 Claims, No Drawings

HOLLOW FIBER MEMBRANE FOR PURIFYING BLOOD

TECHNICAL FIELD

The present invention relates to a high performance blood purification membrane having excellent dialysis performance and allowing little elution from the membrane and little adhesion of blood proteins and platelets and to a method for manufacturing the membrane.

BACKGROUND ART

Progress of the technology utilizing membranes having selective permeability has been remarkable in recent years. Such membranes are used in practice in an extensive field as a gas-liquid separation filter and as hemodialysis equipment, blood filter equipment, and a filter for selective separation of blood components in the medical field.

As materials for the membrane, polymers such as cellulose (regenerated cellulose, cellulose acetate, chemically modified cellulose, etc.), polyacrylonitrile, polymethylmethacrylate, polysulfone, polyethylene vinyl alcohol, polyamide, and the like have been used.

Of these polymers, polysulfone-based polymers have attracted attention as materials for semipermeable membranes due to their characteristics of improving hemocompatibility if the membranes are produced from a raw material polymer solution comprising a hydrophilicity promoter, in addition to the excellent heat stability, acid resistance, and alkali resistance.

Membranes must be dried to fabricate a module by causing the membranes to adhere. Porous membranes made from an organic polymer, particularly dialysis membranes and ultrafilter membranes made from a hydrophobic polymer such as polysulfone-based polymer and the like, are known to exhibit significantly reduced water permeability when dried after preparation as opposed to before drying. For this reason, the membranes must always be handled under wet conditions or under the conditions in which the membranes are dipped in water.

The countermeasure that has conventionally been adopted is a method of filling vacant pores in prepared porous membranes with a low-volatile organic liquid such as glycerol before drying. However, since a low-volatile organic liquid is generally highly viscous, removing such an organic liquid by washing the membrane is time-consuming. After washing modules formed from the membrane, eluted substances originating from the low-volatile organic liquid (various derivatives produced by chemical reactions with the low-volatile organic liquid) were existed in a module enclosure solution.

As a method for drying without using a low-volatile organic liquid, JP-A-6-277470 discloses a method of using an inorganic salt, such as calcium chloride and the like, instead of the low-volatile organic liquid. However, the method still requires washing to remove the inorganic salt. Anxiety remains about an adverse effect that the remaining inorganic salt, even in a very small quantity, may have on dialysis patients.

JP-A-8-52331 and JP-B-8-9668 disclose hydrophilic membranes containing polyvinyl pyrrolidone dried without using a low-volatile organic liquid. The patent specifications describe performance of the membranes for separating plasma components from blood. Permeability of plasma proteins, however, indicates that the membranes do not exhibit dialysis performance. In addition, since the patent specifications do not describe the membrane forming conditions, a third party cannot reproduce the membranes by experiments. The membrane structure itself is also not clear. In addition, the membranes are heated in the drying step at a temperature causing decomposition or denaturation of polyvinyl pyrrolidone. The method is thus extremely undesirable from the viewpoint of decreasing elution from the membranes.

JP-A-6-296686 discloses a hollow fiber membrane of which the inner surface of the membrane directly coming into contact with blood has a polyvinyl pyrrolidone content of about 20–50%. This hollow fiber membrane is mainly to provide a wet membrane to which blood proteins, platelets, and the like adhere in a reduced amount. Therefore, a low-volatile organic liquid such as glycerol must be adhered to prevent a decrease in performance due to drying. The module manufactured from the resultant membrane still contains components that allow elution. In addition, the patent specification does not disclose at all the dialysis performance such as low albumin permeability.

Furthermore, JP-A-2000-300663 and JP-A-2001-205057 disclose methods for manufacturing hollow fibers without using a membrane pore holding agent. The patent specifications do not describe dialysis performance of the resulting membranes. The technological correlation between the manufacturing methods and the characteristics of resultant dry membranes is not clear in these patent specifications.

DISCLOSURE OF THE INVENTION

As discussed above, neither a dry blood purification membrane exhibiting desired dialysis performance prepared without using a membrane pore holding agent that causes elution from a module nor a method for producing such a membrane has been provided heretofore. The reason has been that if the membrane is dried without using a membrane pore holding agent, the membrane can exhibit only very low performance, which is quite different from the performance exhibited under wet conditions. Specifically, the membrane pore holding agent prevents decrease in the membrane performance due to drying. Since the membrane performance decreases to the extent that almost no water permeability can be obtained if the membrane pore holding agent is not used, drying without using the membrane pore holding agent has been inconceivable in a method of manufacturing a membrane having dialysis performance. Based on an idea of previously preparing a wet membrane with specific performance, having higher water permeability and larger pore size than the targeted performance, and producing the target membrane by drying and constricting this previously prepared membrane, that had never been thought of by anyone heretofore, the inventors of the present invention conducted extensive studies. As a result, the present inventors were successful in obtaining a membrane exhibiting excellent selective permeability and having excellent dialysis performance, and allowing little elution from the membrane and little adhesion of blood proteins and platelets.

Therefore, an object of the present invention is to provide a high performance blood purification membrane having excellent dialysis performance and allowing little elution from the membrane and little adhesion of blood proteins and platelets.

A further object of the present invention is to provide a method of preparing such a blood purification membrane.

The above and other objects, features, and advantages of the present invention will become apparent from the following detailed description and the appended claims.

According to the present invention, a hollow fiber blood purification membrane allowing little elution can be obtained by previously preparing a wet membrane having high water permeability and large pore size that does not contain a membrane pore holding agent, and by constricting the pore size by drying the wet membrane after removing a solvent.

The basic features and various preferred embodiment of the present invention will now be given for assisting better understanding of the present invention.

1. A hollow fiber blood purification membrane allowing little elution, which is a dry membrane containing no membrane pore holding agent, obtained by previously preparing a wet membrane containing no membrane pore holding agent and having high water permeability and large pore size and constricting the pore size by drying the wet membrane after removing a solvent.

2. The hollow fiber blood purification membrane described in 1 above, which is a dry membrane containing no membrane pore holding agent prepared by providing a wet membrane made from a material comprising polysulfone-based polymer and polyvinyl pyrrolidone, which does not contain a membrane pore holding agent and has a pure water permeability of not less than 100 mL/(m$^2$·hr·mmHg), permeability of polyvinyl pyrrolidone with a weight average molecular weight of 40,000 of more than 75%, and permeability of albumin in bovine blood plasma of not less than 0.3%, and drying the wet membrane at a temperature of not more than 120° C., the dry membrane:

(a) having a sponge-like structure with the pore size continuously decreasing from the outer surface of the membrane toward the compact layer of the inner surface, (b) having pure water permeability of 10–1,000 mL/(m$^2$·hr·mmHg), (c) having polyvinyl pyrrolidone (weight average molecular weight of 40,000) permeability of not more than 75%, (d) having permeability of albumin in bovine blood plasma of less than 0.3%, (e) having an absorbance in a membrane elution test solution of less than 0.04 and not containing a membrane pore holding agent in the elution test solution, and (f) comprising a polysulfone-based polymer and polyvinyl pyrrolidone, with a polyvinyl pyrrolidone content of 30–45 wt % on the inner surface of the membrane.

3. The blood purification membrane described in 1 or 2 above, containing polyvinyl pyrrolidone insoluble in water.

4. A method for preparing a hollow fiber blood purification membrane allowing little elution, which is a dry membrane containing no membrane pore holding agent, the method comprising previously preparing a wet membrane containing no membrane pore holding agent and having high water permeability and large pore size and constricting the pore size by drying the wet membrane after removing a solvent.

5. The method for preparing the hollow fiber blood purification membrane described in 4 above, wherein the method comprises providing a wet membrane made from a material comprising polysulfone-based polymer and polyvinyl pyrrolidone, which does not contain a membrane pore holding agent and has a pure water permeability of 100 mL/(m$^2$·hr·mmHg), permeability of polyvinyl pyrrolidone with a weight average molecular weight of 40,000 of more than 75%, and permeability of albumin in bovine blood plasma of not less than 0.3%, and drying the wet membrane at a temperature of not more than 120° C., and the dry membrane:

(a) having a sponge-like structure with the pore size continuously decreasing from the outer surface of the membrane toward the compact layer of the inner surface, (b) having a pure water permeability of 10–1,000 mL/(m$^2$·hr·mmHg), (c) having a polyvinyl pyrrolidone (weight average molecular weight of 40,000) permeability of not less than 75%, (d) having permeability of albumin in bovine blood plasma of less than 0.3%, (e) having an absorbance in a membrane elution test solution of less than 0.04 and not containing a membrane pore holding agent in the elution test solution, and (f) comprising polysulfone-based polymer and polyvinyl pyrrolidone, with a polyvinyl pyrrolidone content of 30–45 wt % on the inner surface of the membrane, the method comprising providing a wet membrane made from a material comprising polysulfone-based polymer and polyvinyl pyrrolidone, which does not contain a membrane pore holding agent and has a pure water permeability of 100 mL/(m$^2$ hr mmHg), permeability of polyvinyl pyrrolidone with a weight average molecular weight of 40,000 of more than 75%, and permeability of albumin in bovine blood plasma of 0.3% or more, and drying the wet membrane at a temperature of 120° C. or less.

6. The method for preparing the wet membrane described in 4 or 5 above, comprising injecting a raw material polymer solution and an inner liquid from double-ring nozzles, causing the injected material to pass through an air gap, and causing the material to coagulate in a coagulation bath, thereby producing a hollow fiber membrane, wherein the ratio of the air gap to the spinning speed is 0.01–0.1 m/(m/min).

7. The method described in 6 above, wherein the raw material polymer solution comprises polysulfone-based polymer, polyvinyl pyrrolidone and solvent, with the ratio of polyvinyl pyrrolidone to the polysulfone-based polymer being 18–27 wt %.

8. The method described in 4–7 above, wherein the membrane is irradiated with radiation after drying.

The hollow fiber blood purification membrane (hereinafter may be referred to simply as "membrane" or "hollow fiber membrane" from time to time) of the present invention will now be described.

The membrane of the present invention is a dry membrane not containing a membrane pore holding agent, does not possess a polymer deficient part where the pore size of the membrane exceeds 10 μm, and has a sponge-like structure with the pore size continuously decreasing from the outer surface of the membrane toward the compact layer of the inner surface.

The hollow fiber membrane of the present invention possesses a structure that continues from one surface of the membrane to the other surface, for example, from the inner surface to the outer surface of the membrane. The section from the outer surface of the membrane toward the compact layer of the inner surface, that is to say, the inner section of the membrane, possesses a mesh structure with a mesh (pore) size of not more than 10 μm without a polymer deficient part where the pore size exceeds 10 μm (large vacant pore or void) In the present invention, this structure is referred to as a sponge-like structure.

In the present invention, the compact layer means a layer in which the void areas (i.e. the pores) of the polymer forming the structure of the membrane in the cross section in the thickness direction are small and which contributes to the fractionating performance of the membrane.

The pores of the mesh network of the inner section of the membrane have an inclined structure in which the pore size continuously decreases from the outer surface of the membrane toward the compact layer of the inner surface in the cross section perpendicular to the length direction of the membrane. Specifically, in the case of several concentric cylindrical surfaces, all having the same central axis extending in the length direction of the hollow fiber membrane, the average pore size in each of these surfaces continuously decreases from the outer surface of the membrane toward the compact layer of the inner surface. When blood comes into contact with the inner surface side of the membrane, if the membrane does not have a structure which the pore size continuously decreases from the outer surface of the membrane toward the compact layer of the inner surface, a sharp fractionating performance cannot be achieved.

The membrane pore holding agent referred to in the present invention is a substance that is filled in the vacant pores of the membrane during the production process up until a drying step to prevent decrease in the performance of the membrane during drying. It is possible to fill the vacant pores of the membrane with the membrane pore holding agent by dipping a wet membrane into a solution comprising the membrane pore holding agent. If the membrane pore holding agent is washed and removed after drying, the membrane can possess the performance equivalent to a wet membrane such as water permeability and rejection rate due to the effect of the membrane pore holding agent. There have been reports that a small amount of the membrane pore holding agent remaining in the membrane and/or the module enclosure solution chemically reacts with the membrane pore holding agent to produce various kinds of derivatives, and these derivatives remain in the membrane. However, since the membrane pore holding agent is not used in the membrane during the production process in the present invention, there are no eluted substances resulting from the membrane pore holding agent.

An absorbance of elution test solution of the membrane of the present invention is less than 0.04, and the test solution does not contain a membrane pore holding agent. Here, the elution test solution is prepared according to the hemodialysis apparatus approval standard, which comprises placing 1.5 g of dry hollow fiber membrane cut into pieces with a length of 2 cm and 150 mL of distilled water for injection in a glass container conforming to the alkali elution test for the injection glass container examination according to the Japanese Pharmacopoeia, heating the mixture at 70±5° C. for one hour, removing the membrane, and adding distilled water to make the total volume 150 mL. The absorbance is measured using ultraviolet absorption spectrum exhibiting the maximum absorption wavelength at 220–350 nm. The hemodialysis apparatus approval standard requires an absorbance of 0.1 or less, whereas the membrane of the present invention can achieved an absorbance of less than 0.04 due to using no membrane pore holding agent. The absence or presence of the membrane pore holding agent can be detected by analyzing the sample obtained by condensing the test solution or removing water from the test solution using a known method, such as gas chromatography, liquid chromatography, differential refractometer, ultraviolet spectrophotometer, an infrared absorptiometric method, a nuclear magnetic resonance spectroscopic method, or elemental analysis.

As examples of the membrane pore holding agent, glycol or glycerol compounds, such as ethylene glycol, propylene glycol, trimethylene glycol, 1,2-butylene glycol, 1,3-butylene glycol, 2-butyne-1,4-diol, 2-methyl-2,4-pentadiol, 2-ethyl-1,3-hexanediol, glycerol, tetraethylyne glycol, polyethylene glycol 200, polyethylene glycol 300, and polyethylene glycol 400; organic compounds, such as sucrose fatty acid ester; and inorganic salts, such as calcium chloride, sodium carbonate and sodium acetate can generally be given.

The membrane of the present invention comprises a polysulfone-based polymer and polyvinyl pyrrolidone, with a polyvinyl pyrrolidone content of 30–45 wt % on the inner surface of the membrane. The hydrophilicity of the inner surface of the membrane with which the blood comes into contact is a key factor in the hemocompatibility of the membrane. When the membrane is a polysulfone-based membrane comprising polyvinyl pyrrolidone (hereinafter abbreviated as "PVP"), the PVP concentration of the inner surface of the membrane is important. If the PVP concentration of the inner surface of the membrane is too low, the inner surface of the membrane exhibits hydrophobic, becomes easy to absorb plasma protein, and the blood is prone to clotting. The hemocompatibility of the membrane becomes poor. On the other hand, if the PVP concentration is too high, the eluted amount of the PVP in the blood increases and has an unfavorable effect on the objective and use of the present invention. Therefore, the PVP concentration of the inner surface of the membrane of the present invention is usually 30–45%, with 33–40% being preferable.

As the polysulfone-based polymer used in the present invention, polysulfone-based polymers possessing the repeating units shown by the following formulas (1) or (2) can be given. In the formulas, Ar represents a di-substituted (para-position) phenyl group, with no particular limitation to the degree of polymerization and molecular weight.

$$—O—Ar—C(CH_3)_2—Ar—O—Ar—SO_2—Ar— \quad (1)$$

$$—O—Ar—SO_2—Ar— \quad (2)$$

The PVP concentration of the inner surface of the membrane is determined by X-ray photoelectron spectroscopy (hereinafter abbreviated as XPS). Specifically, the sample is placed on double-sided tape, is cut in the axial direction of the fibers and spread open to expose the inside of the membrane, then XPS measurement is conducted using an ordinary method. The PVP concentration is determined from the nitrogen concentration (nitrogen atom concentration) on the surface and the sulfur concentration (sulfur atom concentration) on the surface and from the area strength of C1s, O1s, N1s, and S2p spectra using a relative sensitivity coefficient appended to the apparatus. When the polysulfone-based polymer has the formula (1), the PVP concentration can be calculated from the following formula (3).

$$\text{PVP concentration (wt \%)} = \frac{C_1 M_1}{C_1 M_1 + C_2 M_2} \times 100 \quad (3)$$

wherein $C_1$: Nitrogen atom concentration (%)
$C_2$: Sulfur atom concentration (%)
$M_1$: Molecular weight of the repeating units of PVP (111)
$M_2$: Molecular weight of the repeating units of polysulfone-based polymer (442)

The membrane of the present invention has a pure water permeability of not less than 10 mL/(m²·hr·mmHg), with not less than 15 mL/(m²·hr·mmHg) being more common. An amount less than 10 mL/(m²·hr·mmHg) is not preferable due to the inferior water removal capability during dialysis. This shows that the membrane of the present invention possesses excellent water permeability even when dried.

In recent hemodialysis treatment methods, membranes allowing sufficient permeation of $\beta_2$-microglobulin (molecular weight: 11,800) which is known to cause dialysis amyloidosis, and possessing a fractionating performance that prevents permeation of nearly all of the albumin (molecular weight: 67,000) have been desired. The membrane of the present invention has a permeability of albumin in bovine blood plasma of not more than 0.3%. If the permeability of the albumin exceeds 0.3%, a great loss in effective albumins in a body occurs. Such high albumin permeability is therefore not preferable for a hemodialysis membrane.

The permeability of albumin in bovine blood serum can be measured using the following method. First, 100 hollow fiber membranes 20 cm long are bundled together to form a small module. Bovine serum containing heparin (heparin amount: 5,000 IU/l, protein concentration: 6.0 g/dL (deciliters)) is heated to 37° C. and passed through the inner surface side of the membrane in the module at a linear speed of 1.0 cm/second to carry out ultrafiltration for 30 minutes with the average input and output pressure of the module being 50 mmHg. The concentrations of the obtained filtrate and the solution before filtering are determined by measuring the absorbance at a wavelength of 280 nm using an ultraviolet spectrophotometer. The permeability is calculated using the following formula (4).

$$\text{Permeability (\%)} = \frac{\text{absorbance of filtrate}}{\text{absorbance of solution before filtering}} \times 100 \qquad (4)$$

A linear functional correlation shown by the following formula (5) is applicable between the permeability of polyvinyl pyrrolidone (A(%)) and the clearance of $\beta_2$-microglobulin (B(mL/min)) in the membrane having a distilled water permeability of 10 mL/(m²·hr·mmHg) or more. Usually, to evaluate the clearance, a dialysis module possessing an effective membrane surface area of 1.5 m² must be prepared. However, the clearance value can be easily speculated using the simple and easy evaluation method of the present invention.

$$B(mL/\text{minute}) = 0.636A + 29.99 \qquad (5)$$

Here, the $\beta_2$-microglobulin clearance is measured by dialysis under the conditions of a 200 mL/minute blood flow rate (inner surface side of the membrane) and a 500 mL/minute dialysis liquid flow rate (outer surface side of the membrane) in a module having an effective area of 1.5 m² in accordance with the standards determined by the Japanese Society for Artificial Organs.

Several factors such as the physical strength of the patient, conditions of the disease, and progress of the disease must be taken into account for the determination of the $\beta_2$-microglobulin clearance. The permeability of polyvinyl pyrrolidone, however, must be below 75% because if the permeability of the polyvinyl pyrrolidone exceeds 75%, the permeability of albumin will exceed 0.3%.

The permeability of polyvinyl pyrrolidone can be measured in the same manner as the permeability of albumin in bovine serum except for using a phosphoric acid buffer (0.15 mol/liter, pH 7.4) aqueous solution comprising 3 wt % of polyvinyl pyrrolidone (K30, manufactured by BASF; weight average molecular weight: 40,000) as the aqueous solution for filtration and regulating the average input and output pressure of the module to 200 mmHg.

Examples of the method for producing the blood purification membrane of the present invention will now be described.

A wet membrane possessing large pores and high water permeability without containing a membrane pore holding agent is prepared beforehand. After removing the solvent, the wet membrane is dried to constrict the pore size. The pore size of the membrane is further constricted by making a portion of the PVP in the membrane insoluble in water. In the method for producing the wet membrane, in which the raw material polymer solution comprising a polysulfone-based polymer (hereinafter referred to simply as "polymer"), polyvinyl pyrrolidone, and a solvent is discharged from a dual ring nozzle and caused to pass through an air gap into a coagulation bath for coagulation. The wet membrane can thus be prepared using an aqueous solution of the polymer solvent as the inner solution. The inner solution is used for producing the hollow spaces and inner surface of the membrane. It is known that the pore size of the inner surface increases in proportion to the solvent concentration of the inner solution. Since the dialysis membrane with the target performance can be obtained by drying and constricting the wet membrane in the present invention, the solvent concentration of the inner solution must be higher than the solvent concentration used for producing a wet membrane possessing the target dialysis performance.

In the present invention, the wet membrane possessing highly water permeability and a large pore diameter is one having a water permeability of 100 mL/(m²·hr·mmHg) or more, a polyvinyl pyrrolidone (weight average molecular weight: 40,000) permeability of more than 75%, and an albumin permeability in bovine serum of not less than 0.3%. The higher the molecular weight of polyvinyl pyrrolidone, the higher the hydrophilicity of the membrane produced from the polyvinyl pyrrolidone. Thus, the larger the molecular weight, a smaller is the amount of the polyvinyl pyrrolidone required for achieving a target effect. For this reason, polyvinyl pyrrolidone with a weight average molecular weight of 900,000 or more is used. If a polyvinyl pyrrolidone having a weight average molecular weight of less than 900,000 is used to give hydrophilic effect to the membrane, a large amount of the polyvinyl pyrrolidone must remain in the membrane thereby causing an increase in the amount of substances eluted from the membrane. On the other hand, if polyvinyl pyrrolidone having a weight average molecular weight of less than 900,000 remaining in the membrane is reduced to decrease the amount of eluted substances in the membrane, the hydrophilic effect becomes insufficient. This causes a decrease in the filtration rate over time during hemodialysis and a sufficient effect cannot be obtained.

The solvent used for dissolving the polysulfone-based polymer and polyvinyl pyrrolidone can dissolve both of these substances, as said solvent N-methyl-2-pyrrolidone, N,N-dimethylformamide, and N,N-dimethyl acetoamide can be given.

There are no specific limitations to the polymer concentration in the raw material polymer solution as long as the concentration allows to produce a membrane, and the membrane obtained has the required properties. The concentration is usually 5–35 wt %, with 10–30 wt % being preferable. In order to attain high water permeability, a low polymer concentration is better. Therefore, a concentration of 10–25 wt % is further preferable.

The amount of polyvinyl pyrrolidone to be added is also important. The mixed ratio of the polyvinyl pyrrolidone to the polymer is usually 27 wt % or less, preferably 10–27 wt %, and particularly preferably 20–27 wt %. If the mixed ratio of the polyvinyl pyrrolidone to the polymer exceeds 27 wt %, the amount of eluted substances tends to increase. If the mixed ratio is below 10 wt %, the viscosity of the raw material polymer solution decreases and it is difficult to obtain a membrane with a sponge-like structure. Fourth components, such as water and a poor solvent, may be added with an objective of controlling the viscosity and dissolution conditions of the raw solution. The type and amount of the fourth components can be appropriately selected based on the combination thereof.

The inner solution is used for producing the hollow spaces and inner surface of the membrane. Water or an aqueous solution of the above solvents can be used as the inner solution.

The air gap is a space between the nozzle and the coagulation bath. The ratio of the air gap (m) to the spinning speed (m/minute) is very important to obtain the membrane of the present invention. This is because the membrane structure of the present invention can be obtained only when the over time phase separation of the raw material polymer solution from the inner surface side to the outer surface side is induced by the contact of non-solvent components in the inner liquid with the raw material polymer solution, and the phase separation from the inner surface side to the outer surface side of the membrane is completed by the time when the raw material polymer solution is fed in the coagulation bath.

The ratio of the air gap to the spinning speed is preferably 0.010–0.1 m/(m/min), and more preferably 0.010–0.05 m/(m/min). If the ratio of the air gap to the spinning speed is less than 0.010 m/(m/min), it is difficult to obtain a membrane possessing the structure and performance of the present invention. If the ratio is more than 0.1 m/(m/min), the tension to the membrane increases so that the membrane may be frequently cut at the air gap point, making the production process difficult.

Spinning speed herein referred to indicates a winding speed of the membrane wound without being stretched during a series of hollow fiber membrane manufacturing operations, in which the raw material polymer solution is injected from nozzles together with the inner liquid, the spun membrane is caused to pass through the air gap and coagulated in the coagulation bath, and the coagulated membrane is wound around a reel. The hollow fiber membrane can be manufactured in a more stable manner by surrounding the air gap using a cylinder or the like and causing gas having a specific temperature and humidity to flow in the air gap at a specific flow rate.

As the coagulation bath, a liquid not dissolving the polymer including, for example, water; alcohols such as methanol and ethanol; ethers; and aliphatic hydrocarbons such as n-hexane and n-heptane, can be used. Of these, water is preferable. It is possible to control the coagulation speed by adding a slight amount of a solvent in which the polymer is soluble to the coagulation bath.

The temperature of the coagulation bath is −30 to 90° C., preferably 0 to 90° C., and still more preferably 0 to 80° C. If the temperature of the coagulation bath is more than 90° C. or less than −30° C., the surface conditions of the hollow-fiber membrane is difficult to be stable in the coagulation bath.

There are no specific limitations to the method of drying after removal of solvent and washing inasmuch as polyvinyl pyrrolidone is not denatured or decomposed. The drying temperature is preferably 120° C. or less, and still more preferably 100° C. or less. If more than 120° C., polyvinyl pyrrolidone may be denatured or decomposed, unpreferably, resulting in an increase in the amount of elution from the dry membrane produced without using a membrane pore holding agent.

Elution from the membrane can be reduced, since a part of PVP in the membrane can be insolubilized in water by irradiating the dry membrane with radiation such as electron beams and the γ-rays. Irradiation may be performed either before or after preparation of the module. In spite of the reduction in the amount of elution, insolubilizing all the amount of PVP in the membrane is undesirable because the leukopenia symptom is observed during dialysis.

PVP insoluble in water in the present invention indicates the amount remaining after subtracting the amount of water-soluble PVP from the total amount of PVP in the membrane. The total amount of PVP in the membrane can be easily calculated by elementary analysis of nitrogen and sulfur. The amount of water-soluble PVP can be determined using the following method.

The amount water-soluble PVP can be determined by completely dissolving the membrane in N-methyl-2-pyrrolidone, adding water to the resulting polymer solution to cause polysulfone polymer to completely precipitate, allowing the polymer solution to stand still, and quantitatively determining the amount of PVP in the supernatant liquid using a liquid chromatography.

BEST MODE FOR CARRYING OUT THE INVENTION

The present invention will be described by examples, which should not be construed as limiting the present invention.

(Measurement of Platelet Adhesion)

The amount of platelet adhesion to the membrane was measured according to the following procedure.

Ten hollow fiber membranes measuring 15 cm in length were bundled together to form a small module. After causing heparin-added fresh human blood to pass through this module at a speed of 1.0 cm/second for 15 minutes, a physiological saline solution was caused to pass through the module for 1 minute. Next, the hollow fiber membrane was cut into 5 mm pieces, placed in a physiological saline solution comprising 0.5% of polyethylene glycol alkylphenyl ether (Triton X-100, manufactured by Wako Pure Chemical Industries, Ltd.), and subjected to ultrasonic irradiation. The lactate dehydrogenase (hereinafter referred to as "LDH") released from the platelets adhered to the surface of the membrane was quantitatively measured to determine the amount of the adhered platelets as the LDH activity per unit area of the membrane (converted to the inner surface area). The enzyme activity was measured using a LDH mono test kit (manufactured by Boehringer Mannheim and Yamanouchi Pharmaceutical Co., Ltd.) As a positive control, a membrane not comprising PVP (obtained by soaking the membrane of Example 1 before exposure to γ-ray irradiation in sodium hypochlorite having an available chlorine concentration of 1500 ppm for 2 days and in ethanol for 1 day) was prepared and compared alongside the membrane of the present invention.

(Amount of Plasma Protein Absorption)

After determining the amount of adsorbed plasma proteins in the same manner as in the determination of the albumin permeability rate, with exception of an ultrafiltration time of 240 minutes, the membrane was washed with a physiological saline solution for one minute. Next, the hollow fiber membrane was cut into 5 mm pieces and stirred in a physiological saline solution comprising 1.0% sodium lauryl sulfate to extract plasma proteins, of which the amount was measured to determine the protein adsorption amount per unit weight of the membrane.

The protein concentration was measured using a BCA Protein Assay (manufactured by Wako Pure Chemical Industries, Ltd. of Japan). As a positive control, a membrane not comprising PVP (obtained by soaking the membrane of Example 1 before exposure to γ-ray irradiation in sodium hypochlorite having an available chlorine concentration of 1500 ppm for 2 days and in ethanol for 1 day) was prepared and compared alongside the membrane of the present invention.

EXAMPLE 1

18.0 wt % of polysulfone (P-1700, manufactured by Amoco Engineering Polymers of the U.S.) and 4.3 wt % of polyvinyl pyrrolidone (K90, manufactured by BASF of Germany; weight average molecular weight: 1,200,000) were dissolved in 77.7 wt % of N,N-dimethyl acetoamide to form a homogenous solution. The mixture ratio of polyvinyl pyrrolidone to polysulfone in the raw material polymer solution was 23.9 wt %. While maintaining the temperature of at 60° C., this raw material polymer solution was discharged from a spinning nozzle (double-ring nozzle, 0.1 mm–0.2 mm–0.3 mm) together with an inner liquid consisting of 30 wt % of N,N-dimethyl acetoamide and 70 wt % of water. The spun membrane was caused to pass through a 0.96 m air gap and sent to a coagulation bath of water at a temperature of 75° C. for soaking.

The path from the spinning nozzle to the coagulation bath is enclosed with a cylindrical tube. The humidity and temperature in this tube was controlled at 54.5% and 51° C., respectively, by circulating nitrogen gas containing steam through the tube. A spinning speed was fixed to 80 m/min. The ratio of the air gap to the spinning speed was 0.012 m/(m/min).

After cutting the wound fiber, the fiber was washed for 2 hours using an 80° C. hot water shower splashed from the upper cut section of the bundle to remove the remaining solvent from the membrane. The membrane was then dried for 7 hours using 87° C. heated wind to obtain a dry membrane having a water content of less than 1%. A portion of the PVP in the membrane was insolubilized by irradiating the obtained dry membrane with γ-rays at 2.5 Mrad.

This membrane does not possess a polymer deficient part with a pore size larger than 10 μm inside the membrane and has a sponge-like structure with the pore size continuously decreasing from the outer surface of the membrane toward the compact layer of the inner surface. The thickness of the compact layer of the inner surface was about 10 μm. The performance of this membrane is shown in Table 1. The $\beta_2$-microglobulin clearance of a module having an effective filtration area of 1.5 m$^2$ formed from this membrane was measured to find that the module possessed a $\beta_2$-microglobulin clearance of 32 mL/min, almost equivalent to the clearance of 32.5 mL/min calculated by applying the PVP permeability to the formula (5). 62% of the entire PVP in the membrane was insoluble in water.

As a result of the elution test of the membrane, the membrane elution test solution was found to exhibit absorbance of 0.04 or less. Since a membrane pore holding agent was not used, no membrane pore holding agent was found in the elution test solution.

As compared with the positive control membrane, this membrane had a lower platelet adhesion amount (positive control membrane: 43.4 Unit/m$^2$) and a lower plasma protein adhesion amount (positive control membrane: 62.5 mg/g).

As can be clearly seen from the above performance, the membrane allows elution in only a very small amount and exhibits only a small amount of blood protein and blood platelet adhesion. In addition, the membrane possesses low albumin permeability and excels in $\beta_2$-microglobulin clearance. The membrane thus also excels in dialysis performance.

EXAMPLE 2

A raw material polymer solution was prepared in the same manner as in Example 1, with the exception of using 4 wt % of polyvinyl pyrrolidone and 78 wt % of N,N-dimethyl acetoamide. The mixture ratio of polyvinyl pyrrolidone to polysulfone in the raw material polymer solution was 22.2 wt %. The performance of this membrane is shown in Table 1.

This membrane not only allows elution only in a very small amount, but also permits adhesion of blood proteins and blood platelet only to a limited extent. In addition, the membrane was found to excel in dialysis performance based on the fact that the membrane exhibits a low albumin permeability and excels in $\beta_2$-microglobulin clearance.

EXAMPLE 3

A raw material polymer solution was prepared in the same manner as in Example 1, with the exception of using 4.8 wt % of polyvinyl pyrrolidone and 77.2 wt % of N,N-dimethyl acetoamide. The mixture ratio of polyvinyl pyrrolidone to polysulfone in the raw material polymer solution was 26.7 wt %. The performance of this membrane is shown in Table 1.

This membrane not only allows elution only in a very small amount, but also permits adhesion of blood proteins and blood platelet only in a small amount. In addition, the membrane was found to excel in dialysis performance based on the fact that the membrane exhibits low albumin permeability and excels in $\beta_2$-microglobulin clearance.

EXAMPLE 4

The same experiment as in Example 3 was conducted except for using a mixed solution of 52 wt % of N,N-dimethyl acetoamide and 48% of water as an inner liquid. The performance of this membrane is shown in Table 1.

This membrane not only allows elution only in a very small amount, but also permits adhesion of blood proteins and blood platelet only in a small amount. In addition, the membrane was found to excel in dialysis performance based on the fact that the membrane exhibits low albumin permeability and excels in $\beta_2$-microglobulin clearance.

COMPARATIVE EXAMPLE 1

With the exception of not using γ-ray irradiation, a membrane was prepared in the same manner as in Example 1. The results are shown in Table 2. The membrane elution test solution was found to exhibit absorbance of more than 0.04 due to elution of PVP.

COMPARATIVE EXAMPLE 2

A raw material polymer solution was prepared in the same manner as in Example 1, with the exception of using 5.0 wt % of polyvinyl pyrrolidone and 77.0 wt % of N,N-dimethyl acetoamide. The mixture ratio of polyvinyl pyrrolidone to polysulfone in the raw material polymer solution was 27.8 wt %. The performance of this membrane is shown in Table 2.

COMPARATIVE EXAMPLE 3

A raw material polymer solution was prepared in the same manner as in Example 1, with the exception of using 3.6 wt % of polyvinyl pyrrolidone and 78.4 wt % of N,N-dimethyl acetoamide. The mixture ratio of polyvinyl pyrrolidone to polysulfone in the raw material polymer solution was 20.0 wt %.

The performance of this membrane is shown in Table 2.

COMPARATIVE EXAMPLE 4

The same experiment as in Example 3 was conducted except for using a mixed solution of 60 wt % of N,N-dimethyl acetoamide and 40% of water as an inner liquid. The performance of this membrane is shown in Table 2.

TABLE 1

|  | Example 1 | Example 2 | Example 3 | Example 4 |
|---|---|---|---|---|
| Internal diameter of membrane (μm) | 195 | 201 | 190 | 193 |
| External diameter of membrane (μm) | 280 | 288 | 282 | 284 |
| Water permeability (mL/(m² · hr · mmHg)) | 20 | 18 | 25 | 390 |
| Permeability of Albumin (%) | not more than 0.01 | not more than 0.01 | not more than 0.01 | 0.25 |
| Permeability of PVP (%) | 4 | 4 | 5 | 72 |
| Concentration of PVP on the inner surface of the membrane (wt %) | 35 | 30 | 44 | 36 |
| Presence of water insoluble PVP | yes | yes | yes | yes |
| Absorbance of elusion test solution | 0.022 | 0.020 | 0.035 | 0.023 |
| Presence of membrane pore holding agent in elution test solution | no | no | no | no |
| Amount of platelet adhesion (LDH-Unit/m²) | 15.5 | 17.5 | 4.2 | 13.8 |
| Amount of plasma protein solution absorption (mg/g) | 2.1 | 5.5 | 1.8 | 2.0 |
| Water permeability of wet membrane before drying (mL/(m² · hr · mmHg)) | 190 | 170 | 260 | 3,100 |
| Permeability of Albumin in wet membrane before drying (%) | 0.32 | 0.34 | 0.35 | 0.51 |
| Permeability of PVP in wet membrane before drying (%) | 77 | 84 | 84 | 99 |

TABLE 2

|  | ComparativeExample | | | | | |
|---|---|---|---|---|---|---|
|  | 1 | 2 | 3 | 4 | 5 | 6 |
| Internal diameter of membrane (μm) | 195 | 200 | 199 | 196 | 200 | 191 |
| External diameter of membrane (μm) | 290 | 298 | 290 | 297 | 291 | 276 |
| Water permeability (mL/(m² · hrmmHg)) | 20 | 35 | 15 | 970 | 8 | 15 |
| Permeability of Albumin (%) | not more than 0.01 | not more than 0.01 | not more than 0.01 | 0.37 | not more than 0.01 | not more than 0.01 |
| Permeability of PVP (%) | 4 | 5 | 4 | 79 | 0 | 4 |
| Concentration of PVP on the inner surface of the membrane (wt %) | 35 | 47 | 28 | 33 | 34 | 36 |
| Presence of water insoluble PVP | no | yes | yes | yes | yes | yes |
| Absorbance of elusion test solution | 0.044 | 0.040 | 0.018 | 0.021 | 0.020 | 0.021 |
| Presence of membrane pore holding agent in elution test solution | no | no | no | no | no | no |
| Amount of platelet adhesion (LDH-Unit/m²) | 15.5 | 3.8 | 19.6 | 15.0 | 15.1 | 16.8 |
| Amount of plasma protein solution absorption (mg/g) | 2.1 | 1.1 | 5.9 | 2.8 | 2.1 | 3.0 |
| Water permeability of wet membrane before drying (mL(m² · hrmmHg)) | 190 | 310 | 130 | 8,600 | 76 | 190 |
| Permeability of Albumin in wet membrane before drying (%) | 0.32 | 0.38 | 0.31 | 0.62 | 0.18 | 0.32 |
| Permeability of PVP in wet membrane before drying (%) | 77 | 85 | 76 | 100 | 52 | 77 |

INDUSTRIAL APPLICABILITY

The membrane of the present invention has excellent dialysis performance and allows very little elution from the membrane and little adhesion of blood proteins and platelets and can be used in medicines, medical treatment, and general industrial use.

The invention claimed is:

1. A hollow fiber blood purification membrane, which is a dry membrane containing no membrane pore holding agent:
   wherein the dry membrane is prepared by:
   (i) providing a wet membrane made from a material polymer solution comprising polysulfone-based polymer and polyvinyl pyrrolidone in a solvent but no membrane pore holding agent, the wet membrane having:
   a pure water permeability of not less than 100 mL/($m^2 \cdot hr \cdot mmHg$), permeability of polyvinyl pyrrolidone with a weight average molecular weight of 40,000 of more than 75%, and permeability of albumin in bovine blood-plasma of not less than 0.3%;
   (ii) removing the solvent;
   (iii) drying the wet membrane without addition of a membrane pore holding agent at a temperature of not more than 120° C. to constrict the pore size, and
   (iv) exposing the dried membrane to radiation, wherein the dry membrane:
   (a) has a sponge-like structure with the pore size continuously decreasing from the outer surface of the membrane toward the compact layer of the inner surface,
   (b) has pure water permeability of 10–1,000 mL/($m^2 \cdot hr \cdot mmHg$),
   (c) has permeability of polyvinyl pyrrolidone with a weight average molecular weight of 40,000 of more than 75%,
   (d) has permeability of albumin in bovine blood plasma of less than 0.3%,
   (e) has an absorbance in a membrane elution test solution of less than 0.04, with no membrane pore holding agent contained in the elution test solution, and
   (f) comprises a polysulfone-based polymer and polyvinyl pyrrolidone, with a polyvinyl pyrrolidone content of 30–45 wt % on the inner surface of the membrane.

2. The blood purification membrane according to claim 1, wherein said polyvinyl pyrrolidone is insoluble in water.

3. A method for preparing a hollow fiber membrane for blood purification, which is a dry membrane containing no membrane pore holding agent:
   wherein the method comprises:
   (i) providing a wet membrane made from a material polymer solution comprising polysulfone-based polymer and polyvinyl pyrrolidone in a solvent but no membrane pore holding agent, the wet membrane having:
   a pure water permeability of not less than 100 mL/($m^2 \cdot hr \cdot mmHg$),
   permeability of polyvinyl pyrrolidone with a weight average molecular weight of 40,000 of more than 75%, and
   permeability of albumin in bovine blood-plasma of not less than 0.3%;
   (ii) removing the solvent;
   (iii) drying the wet membrane without addition of a membrane pore holding agent at a temperature of not more than 120° C. to constrict the pore size, and
   (iv) exposing the dried membrane to radiation;
   and the dry membrane prepared so that it:
   (a) has a sponge-like structure with the pore size continuously decreasing from the outer surface of the membrane toward the compact layer of the inner surface,
   (b) has a pure water permeability of 10–1,000 mL/($m^2 \cdot hr \cdot mmHg$),
   (c) has permeability of polyvinyl pyrrolidone with a weight average molecular weight of 40,000 of more than 75%,
   (d) has permeability of albumin in bovine blood plasma of less than 0.3%,
   (e) has an absorbance in a membrane elution solution test solution of less than 0.04, with no membrane pore holding agent contained in the elution test solution, and
   (f) comprises a polysulfone-based polymer and polyvinyl pyrrolidone, with a polyvinyl pyrrolidone content of 30–45 wt % on the inner surface of the membrane.

4. The method for preparing the wet membrane according to claim 3, comprising injecting a raw material polymer solution and an inner liquid from double-ring nozzles, causing the injected material to pass through an air gap, and causing the material to coagulate in a coagulation bath, thereby producing a hollow fiber membrane, wherein the ratio of the air gap to the spinning speed is 0.01–0.1 m/(m/min).

5. The method according to claim 4, wherein the raw material polymer solution comprises a polysulfone-based polymer, polyvinyl pyrrolidone and solvent, with the ratio of polyvinyl pyrrolidone to the polysulfone-based polymer in an amount of percentages equivalent to 18–27 wt % of polyvinyl pyrrolidone to polysulfone-based polymers.

6. The method according to claim 5, wherein the membrane is irradiated with radiation after drying.

7. The method according to claim 4, wherein the membrane is irradiated with radiation after drying.

8. The method according to claim 3, wherein the membrane is irradiated with radiation after drying.

9. A hollow fiber membrane for blood purification, comprising a dry membrane containing no membrane pore holding agent:
   wherein the dry membrane comprises:
   a sponge-like structure with the pore size continuously decreasing from the outer surface of the membrane toward the compact layer of the inner surface,
   pure water permeability of 10–1,000 mL/($m^2 \cdot hr \cdot mmHg$),
   permeability of polyvinyl pyrrolidone with a weight average molecular weight of 40,000 of more than 75%,
   permeability of albumin in bovine blood plasma of less than 0.3%,
   an absorbance in a membrane elution solution test solution of less than 0.04, with no membrane pore holding agent contained in the elution test solution, and
   a polysulfone-based polymer and polyvinyl pyrrolidone, with a polyvinyl pyrrolidone content of 30–45 wt % on the inner surface of the membrane.

10. The hollow fiber membrane according to claim 9, wherein said dry membrane has a water content of less than 1%.

* * * * *